United States Patent [19]

McCarthy, Jr. et al.

[11] 3,975,433
[45] Aug. 17, 1976

[54] 1-(2,4-DIMETHOXY-PHENYL)-3-(2-HYDROXYETHYL)THIOUREA

[75] Inventors: James R. McCarthy, Jr., Midland; Don V. Wysong, Farwell; Bobbie J. Allen, Midland, all of Mich.

[73] Assignee: The Dow Chemical Company, Midland, Mich.

[22] Filed: Sept. 15, 1975

[21] Appl. No.: 613,661

Related U.S. Application Data

[63] Continuation-in-part of Ser. No. 438,927, Feb. 1, 1974, abandoned.

[52] U.S. Cl. ............................ 260/552 R; 424/322; 260/453 AR
[51] Int. Cl.$^2$ .............. C07C 157/05; C07C 157/09
[58] Field of Search .................. 260/552 R; 424/322

[56] References Cited
UNITED STATES PATENTS 3,767,816  10/1973  Moss et al. ........................ 424/322
3,891,769  6/1975  Shea et al. ........................ 424/322

FOREIGN PATENTS OR APPLICATIONS 1,356,908  12/1959  France

OTHER PUBLICATIONS

Kharida et al., CA 55: 10372f (1961).
Schroeder, Chem. Reviews 55, pp. 181–189, (1955).
Index Chemicus, vol. 43, Issue 41, 1971, 184, 408.

Primary Examiner—Robert V. Hines
Assistant Examiner—Thomas A. Waltz
Attorney, Agent, or Firm—James W. Ambrosius; Gary D. Street

[57] ABSTRACT 1-(2,4-Dimethoxyphenyl)-3-(2-hydroxyethyl)thiourea is useful as an antidepressant and as a parasiticide.

1 Claim, No Drawings

1-(2,4-DIMETHOXY-PHENYL)-3-(2-HYDROXYETHYL)THIOUREA

This application is a continuation-in-part of applicants' prior application Ser. No. 438,927, filed on Feb. 1, 1974, now abandoned.

BACKGROUND OF THE INVENTION

The present invention relates to the pharmaceutical field, and more particularly to the novel compound 1-(2,4-dimethoxyphenyl)-3-(2-hydroxyethyl)thiourea (for convenience, hereinafter referred to as "thiourea") which is useful as an antidepressant and as a parasiticide.

Various thioureas are described in the prior art. See, for example, U.S. Pat. No. 3,767,816; French patent 1,356,908 and Schroeder, Chem. Reviews 55, 181–189 (1955), Chem. Abstracts 55:10372f and 1582d (1960), Index Chemicus, Vol. 43, Issue 41, 1971, 184408. None of these references disclose the compound of the present invention or its activity as an antidepressant and parasiticide.

SUMMARY OF THE INVENTION

The novel compound 1-(2,4-dimethoxyphenyl)-3-(2-hydroxyethyl)thiourea of the present invention is illustrated by the formula:

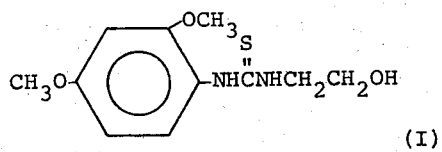

(I)

The compound of the present invention has valuable antidepressant properties at non-toxic dosage levels and also shows an activity in the control of *Ascaridia galli* in chickens. The compound is normally a crystalline solid at ambient temperatures and is ordinarily administered to mammals in doses of from about one to about 50 or more milligrams per kilogram of body weight.

DESCRIPTION OF THE PREFERRED EMBODIMENTS

The thiourea compound can be administered internally, i.e., parenterally or orally, and can be formulated into various pharmaceutical dosage forms such as tablets, capsules, solutions, suspensions, pills and the like, for immediate or sustained release by combining the active compound with suitable pharmaceutically acceptable carriers or diluents according to methods well known in the art. Such dosage forms may additionally include excipients, binders, fillers, flavoring and sweetening agents, and other therapeutically inert ingredients necessary in the formulation of the desired pharmaceutical preparation.

In one preferred utility, the thiourea of the present invention provides a new effective antidepressant. This is surprising and unexpected since many compounds of closely related structure do not exhibit antidepressant activity.

The compound can be prepared by the addition of ethanolamine to a selected aryl isothiocyanate reactant. The reactants are known and can be obtained commercially or prepared according to known literature methods. The reaction is usually carried out by mixing the isothiocyanate reactant with a suitable reaction carrier medium, such as, for example, alcohols, benzene, acetone, dimethylformamide or other suitable carriers, and adding thereto a mixture of the ethanolamine reactant in a similar carrier. Generally, equimolar proportions of the reactants are employed. The ethanolamine reactant mixture is usually added dropwise, with agitation, to the isothiocyanate reactant mixture while maintaining the temperature of the resulting reaction mixture below about 50°C. Following the completion of the ethanolamine addition, the reaction mixture is stirred for a period of from about 1 to about 18 hours. The resulting solid product precipitate is recovered from the reaction mixture by filtration, dried, and recrystallized if desired from a suitable solvent, such as hereinbefore mentioned. Where the product precipitate is not formed in the reaction mixture, the same can be concentrated, as by evaporation, for example, and the residue obtained is dissolved in a solvent and the solution cooled to obtain the desired product.

The compound has also shown activity in the control of *Ascaridia galli* in chickens. This activity is surprising and unexpected since several related compounds do not exhibit such activity.

The following examples further illustrate the present invention.

EXAMPLE 1

1-(2,4-methoxyphenyl)-3-(2-hydroxyethyl)thiourea 2,4-Dimethoxyphenylisocyanate (27.9 grams; 0.14 mole) was mixed with 35 ml of isopropyl alcohol and a solution of ethanolamine (9.32 grams; 0.14 mole) in 35 ml of isopropyl alcohol added thereto dropwise over a 10 minute period. During the addition, the reaction mixture temperature was maintained below about 50°C. Following the completion of the ethanolamine addition, the reaction mixture was stirred for a period of about two hours and then allowed to stand at ambient temperatures for a period of about 16 hours. The reaction mixture was then filtered to recover the crystalline product precipitate formed therein. The product was washed with isopropyl alcohol and dried to obtain about an 82% yield of the title compound as a brown crystalline solid having a melting point of 160°–162°C.

The antidepressant properties of the thiourea employed in the methods of the present invention are determined by measuring their ability to counteract ptosis induced in animals by the intraperitoneal injection of reserpine. Graded doses (from about 2.1 to about 100 mg/kg) of the active compounds of this invention are administered intraperitoneally to groups of five mice each, followed 30 minutes later by an intraperitoneal injection of reserpine in an amont which is known to induce ptosis in mice. Similar groups of control mice are administered only reserpine. Forty-five minutes after the administration of reserpine, the presence or absence of ptosis is noted. The percent inhibition of ptosis is noted and the median effective dose ($ED_{50}$) of each test ingredient which protected 50% of the test mice from reserpine-induced ptosis was calculated. In such operations, the median $ED_{50}$'s were established for the test compound as set forth in the following table.

TABLE I

| Cmpd. No. | Test Material | ED₅₀ i.p. |
|---|---|---|
| 1. | 1-(2,4-dimethoxyphenyl)-3-(2-hydroxyethyl)thiourea | 38.0 |
| 2. | *Imipramine | 15.0 |
| 3. | *Doxepin | 27.0 |

*Reference Drugs

In comparative trials employing related compounds 1-(2-methoxyphenyl)-3-(2-hydroxyethyl)thiourea and 1-(3,4-dimethoxyphenyl)-3-(2-hydroxyethyl)thiourea, respectively, it was found that such compounds did not inhibit reserpine-induced ptosis at dosages of 60 mg/kg (i.p.).

The treatment of depression in accordance with this invention comprises administering internally to an animal a compound as represented by formula, Table I, usually combined with a pharmaceutical excepient or carrier, in an amount sufficient to produce an antidepressant effect. Preferably, the compounds are administered orally. Advantageously, equal doses will be administered from 1 to 6 times daily.

The dosage required to achieve antidepressant activity in the animal will vary with various factors such as the species of animals, general health and tolerances of the animal, weight, sex and age of the animal, the nature and severity of the disease being treated and the like. Generally, a total daily dosage would be in the range of from about 0.5 to about 100.0 or more milligrams per kilogram of body weight, usually from 1.0 to about 25.0 or more milligrams per kilogram of body weight.

The following example is illustrative of the compound of the present invention.

EXAMPLE 2

The following ingredients are combined:

| | Parts |
|---|---|
| 1-(2,4-dimethoxyphenyl)-3-(2-hydroxyethyl)thiourea | 40 |
| Peanut oil | 60 |

The combination is thoroughly mixed into a thick slurry. It can then be put into soft gelatin capsules.

For parenteral application the invention can be dispersed in sterile aqueous suspension or dissolved in a pharmacologically acceptable oil or oil-water emulsion. Suitable excipients can also be added.

EXAMPLE 3

The compound was evaluated for activity in the control of *Ascaridia galli* in chickens. The test chickens following infection with Ascaridia are held for at least 30 days to permit all worms to mature. The compound is evaluated for activity in two chickens which are caged together. The compound may be administered orally as a single oral dose or in the feed for four consecutive days. Anthelmintic efficacy of the compound against Ascaridia is determined by comparing the number of ascarids passed in the feces during the first 72 hours post treatment to the number of worms recovered at necropsy.

At a dose of 150 mg/kg the new compound 1-(2,4-dimethoxyphenyl)-3-(2-hydroxyethyl)thiourea showed a 50% activity when the number of worms passed in the feces was compared to those found at autopsy. The following compounds were also tested as controls and found to have no activity in controlling Ascaridia: 1-(4-methoxyphenyl)-3-(2-hydroxyethyl)thiourea; 1-(2,4-dimethylphenyl)-3-(2-hydroxyethyl)thiourea; 1-(4-methylphenyl)-3-(2-hydroxyethyl)thiourea; and 1-(4-methoxy-2-methylphenyl)-3-(2-hydroxyethyl)thiourea.

In view of the above, it will be seen that the several objects of the invention are achieved and other advantageous results attained.

As various changes could be made without departing from the scope of the invention it is intended that all matter contained in the above description shall be interpreted as illustrative and not in a limiting sense.

That which is claimed is:
1. The compound 1-(2,4-dimethoxyphenyl)-3-(2-hydroxyethyl)thiourea.

* * * * *